United States Patent
Akiba

(10) Patent No.: US 6,752,755 B2
(45) Date of Patent: Jun. 22, 2004

(54) ENDOSCOPE AND ENDOSCOPE CAP WITH RECESSED FOCAL POINT

(75) Inventor: Haruo Akiba, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/915,264

(22) Filed: Jul. 27, 2001

(65) Prior Publication Data

US 2002/0032367 A1 Mar. 14, 2002

(30) Foreign Application Priority Data

Aug. 7, 2000 (JP) ........................................ 2000-238617
Aug. 7, 2000 (JP) ........................................ 2000-238618

(51) Int. Cl.[7] .............................. A61B 1/04; A61B 1/00
(52) U.S. Cl. ...................... 600/127; 600/129; 600/188
(58) Field of Search .............................. 600/127, 121, 600/125, 129, 123, 153, 156, 157, 158, 203, 187, 205, 188

(56) References Cited

U.S. PATENT DOCUMENTS

| | | | |
|---|---|---|---|
| 3,643,653 A | * 2/1972 | Takahashi et al. | 600/129 |
| 3,980,078 A | * 9/1976 | Tominaga | 600/157 |
| 4,219,013 A | 8/1980 | Okada | |
| 4,491,865 A | 1/1985 | Danna et al. | |
| 4,794,911 A | * 1/1989 | Okada | 600/127 |
| 5,002,042 A | 3/1991 | Okada | |
| 5,447,148 A | * 9/1995 | Oneda et al. | 600/131 |
| 5,518,501 A | * 5/1996 | Oneda et al. | 600/127 |
| 5,685,823 A | * 11/1997 | Ito et al. | 600/127 |
| 5,746,695 A | * 5/1998 | Yasui et al. | 600/127 |
| 5,895,350 A | * 4/1999 | Hori | 600/167 |
| 5,897,487 A | * 4/1999 | Ouchi | 600/127 |
| 5,989,185 A | * 11/1999 | Miyazaki | 600/175 |
| 6,059,719 A | * 5/2000 | Yamamoto et al. | 600/127 |
| 6,086,583 A | * 7/2000 | Ouchi | 606/41 |
| 6,095,970 A | * 8/2000 | Hidaka et al. | 600/110 |
| 6,142,932 A | * 11/2000 | Morizumi | 600/166 |
| 6,251,068 B1 | * 6/2001 | Akiba et al. | 600/182 |
| 6,306,081 B1 | * 10/2001 | Ishikawa et al. | 600/127 |
| 6,409,658 B1 | * 6/2002 | Mitsumori | 600/167 |
| 6,464,708 B1 | * 10/2002 | Higuma et al. | 606/140 |
| 2003/0088154 A1 | * 5/2003 | Ishibiki et al. | 600/127 |

FOREIGN PATENT DOCUMENTS

| | | | |
|---|---|---|---|
| JP | 10-248792 | 9/1998 | |
| JP | 10248792 A | * 9/1998 | ............ A61B/1/00 |
| JP | 10328202 A | * 12/1998 | ........... A61B/17/39 |
| JP | 11-342104 | 12/1999 | |
| JP | 11-342105 | 12/1999 | |

* cited by examiner

*Primary Examiner*—Henry Bennett
*Assistant Examiner*—Kathryn Odland
(74) *Attorney, Agent, or Firm*—Oliff & Berridge, PLC

(57) ABSTRACT

A cap of an endoscope has an end part. On an inner periphery of the end part, a reference mark showing an ideal focus position and six marks are formed with regular intervals. When a circular end surface of the cap is pressed against a mucous membrane, the mucous membrane swells to the reference mark. Therefore, the mucous membrane can be kept at the ideal focus position for an object optical system.

5 Claims, 4 Drawing Sheets

F I G. 1
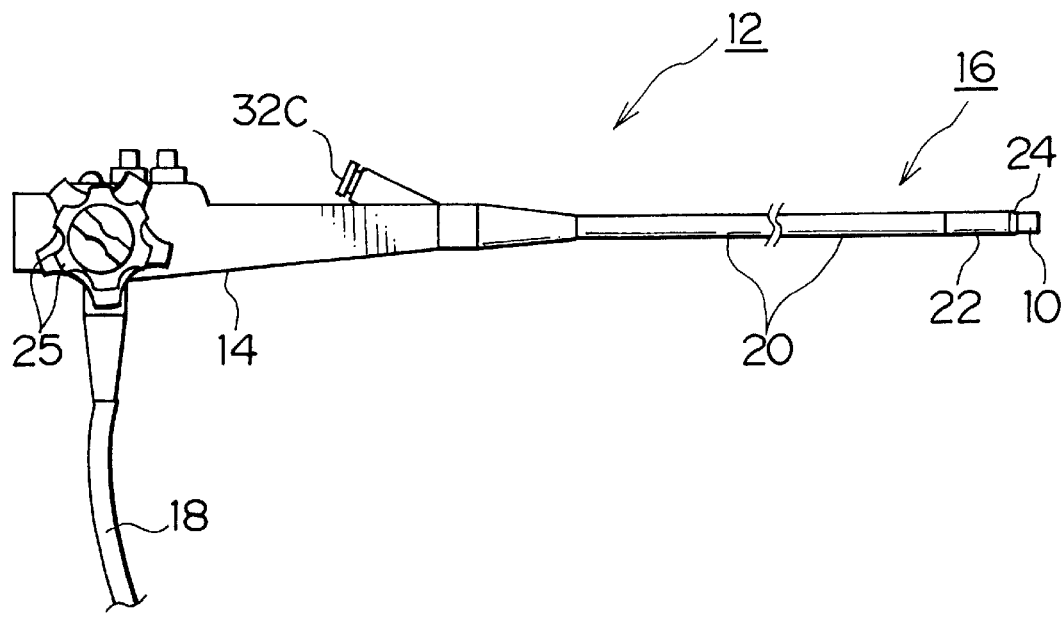
F I G. 2
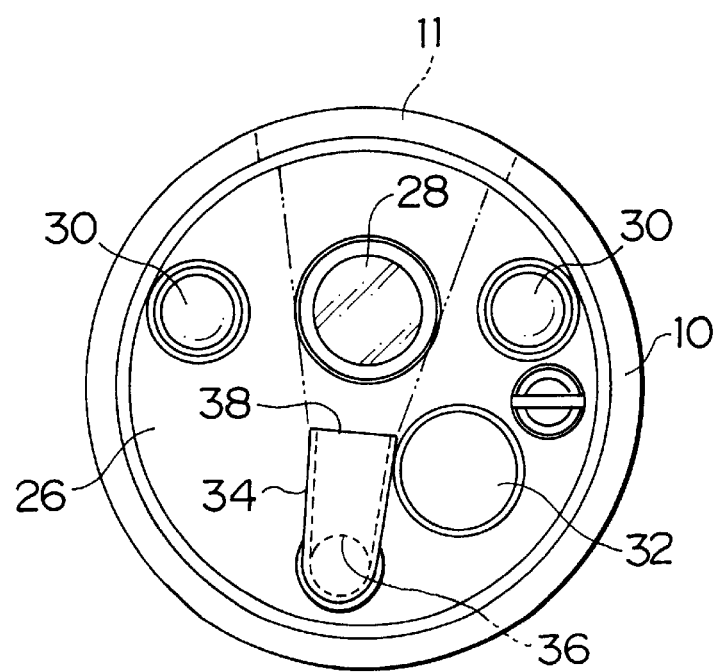

ENDOSCOPE AND ENDOSCOPE CAP WITH RECESSED FOCAL POINT

BACKGROUND OF THE INVENTION

1. Field of the Invention

The present invention generally relates to an endoscope that has an object optical system with a variable focal length at the end of an insertion part. The present invention also relates to an endoscope cap that is fitted on a distal end of an insertion part of a medical endoscope.

2. Description of the Related Art

An endoscope that magnifies a mucous membrane like a microscope can change a depth of focus (observation distance). When a focal length of an object optical system is large, the depth of focus is small. When the object is not completely in the ideal position, it is out of focus.

Japanese Patent Application Laid-open No. 11-342104 discloses a zoom endoscope that has a cap fitted on a distal end of an insertion part to maintain the distance between the object and an object optical system appropriate. The endoscope sets the end of the cap as the ideal focus position for the object optical system, and puts the end of the cap in contact with the mucous membrane to position the mucous membrane at the ideal focus position.

Each of the caps disclosed in Japanese Patent Application Laid-open Nos. 10-248792 and 11-342105 is cylindrically shaped and composed of a peripheral part and an end part. The peripheral part is fitted on the outer periphery of the distal end, and the end part is a predetermined length from the end of the distal end and comes in contact with the object. Since the distance between the object and an object optical system in the distal end is constant, the object optical system can be focused on the object when the predetermined length is appropriately set.

In the zoom endoscope of Japanese Patent Application Laid-open No. 11-342104, however, when the cap is in contact with the mucous membrane, it goes out of focus due to the pulsation motion of the patient and all other movement.

After the cap is fitted, a step is formed between the peripheral part and the end part. Thus, the cap is lodged in the patient's body when the insertion part is inserted into or drawn from the body, and this may cause pain or discomfort to the patient.

In case of the cap of Japanese Patent Application Laid-open No. 11-342105, there is a large step between the peripheral part and the distal end. The cap is also lodged in the body.

SUMMARY OF THE INVENTION

The present invention has been developed in view of the above-described circumstances, and has as its object the provision of an endoscope that can be focused on an object without being affected by pulsation motion of a patient and all other movement.

The present invention has been developed in view of the above-described circumstances, and has as its object the provision of an endoscope cap that does not have a step after it is fitted so that an insertion part of an endoscope can be smoothly inserted into and drawn from a patient's body.

In order to achieve the above-described object, the present invention is directed to an endoscope with an object optical system that can change a focal length in a distal end of an insertion part, wherein: an ideal focus position for the object optical system is a predetermined length behind of an end of a cap fitted on an outer periphery of the distal end of the insertion part.

According to the invention, the position to which the object swells when the cap is pressed against it is set as the ideal focus position. Thus, the object optical system can be focused on the object without being affected by the pulsation motion of the patient and all other movement.

A section of an edge part of the end of the cap is ark-shaped with the radius of curvature of the predetermined length. The object is not damaged even when the edge part is pressed against the object.

Marks for various magnifications are formed on an inner periphery of the cap. The end of the insertion part is put on one of the marks for a corresponding magnification.

In order to achieve the above-described object, the present invention is directed to an endoscope cap that is fitted on an outer periphery of a distal end of an insertion part of an endoscope, wherein: the endoscope cap is composed of a peripheral part that is on the outer periphery of the distal end and an end part that comes in contact with an object; the peripheral part is thinner than the end part; an outer diameter of the peripheral part is smaller than an outer diameter of the end part before the endoscope cap is fitted; and the outer diameter of the peripheral part is substantially the same as the outer diameter of the end part after the endoscope cap is fitted.

According to the invention, the outer diameter of the peripheral part is smaller than that of the end part before the cap is fitted, and the outer diameter of the peripheral part is substantially the same as that of the end part after the cap is fitted. Thus, there is no step between the peripheral part and the end part, and the insertion part of the endoscope can be smoothly inserted into and drawn from the patient's body.

In addition, the end part is softer than the peripheral part, and the end part softly comes in contact with the object. Thus, the object is not damaged, even when the end part is pressed against the object. Since the peripheral part is harder than the end part, the peripheral part is firmly fitted on the end of the insertion part.

BRIEF DESCRIPTION OF THE DRAWINGS

The nature of this invention, as well as other objects and advantages thereof, will be explained in the following with reference to the accompanying drawings, in which like reference characters designate the same or similar parts throughout the figures and wherein:

FIG. 1 is a view of an endoscope;

FIG. 2 is a front view of a distal end of the endoscope in FIG. 1;

DETAILED DESCRIPTION OF THE PREFERRED EMBODIMENTS

Figure 3:
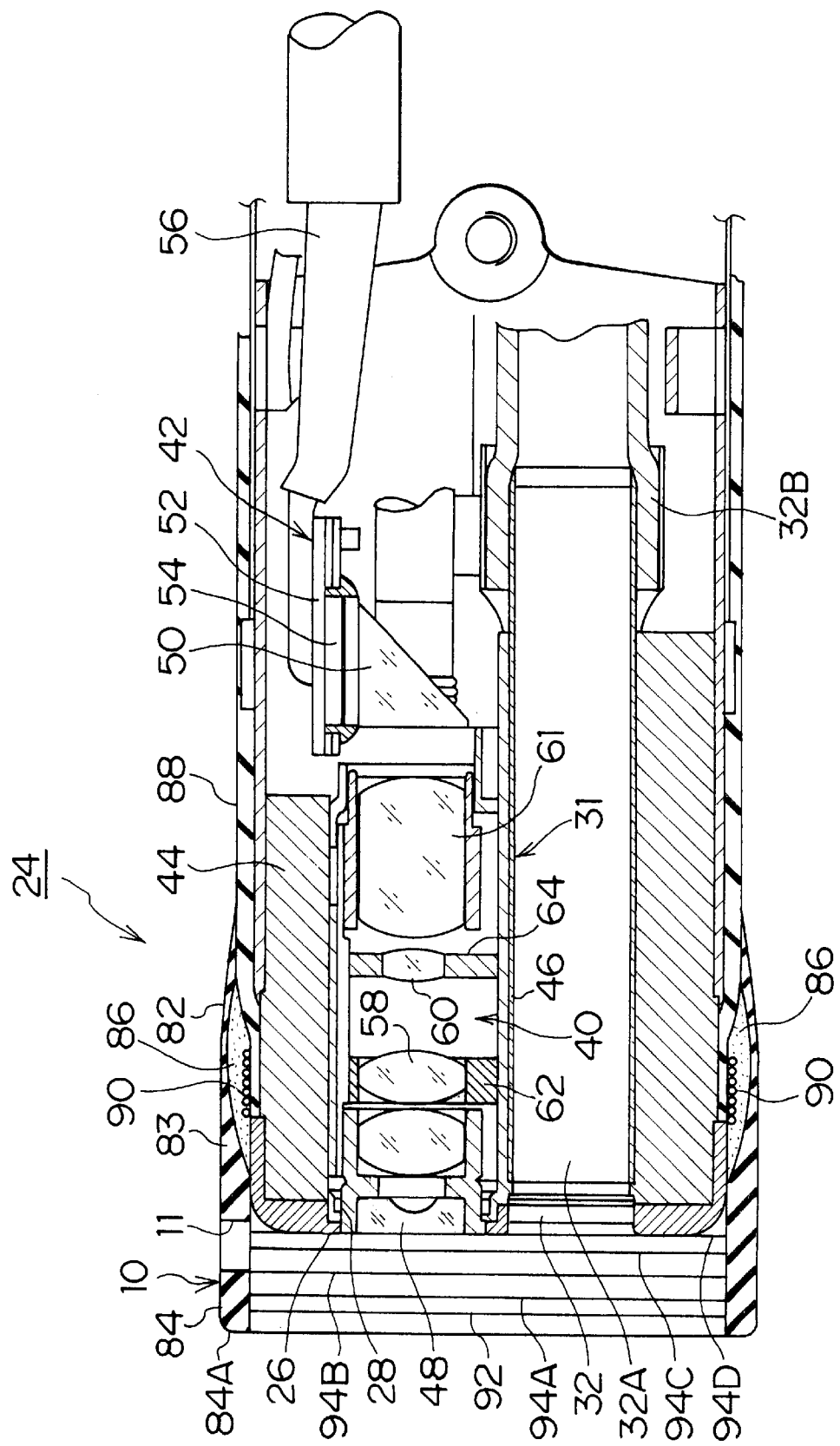
FIG. 3 is a section of the distal end of the endoscope in FIG. 1.

Hereunder a preferred embodiment of the present invention will be described in accordance with the accompanied drawings.

FIG. 1 is a view of an endoscope 12 with a cap 10. The endoscope 12 has a hand control part 14, which an operator holds and controls. The hand control part 14 is connected to an insertion part 16 inserted into a patient's body, and is connected with a universal code 18 connected to a processor (not shown).

The insertion part 16 is mainly composed of a flexible part 20, and a bending part 22 is connected to the end of the flexible part 20, and a distal end 24 is connected to the end of the bending part 22. The cap 10 is fitted on the distal end 24. The bending part 22 changes a direction of the distal end 24, and the operator rotates an angle knob 25 of the hand control part 14 to change the direction.

As shown in FIG. 2, an observation window 28 is provided in the center of an end surface 26 of the distal end 24, and illumination windows 30 are provided on both sides of the observation window 28. The observation window 28 and the illumination windows 30 are flush with the end surface 26.

The observation window 28 is connected with an object lens unit 31 shown in FIG. 3, and the illumination windows 30 are connected with light guides (not shown). A tool guide opening 32 for tools including forceps is formed in the end surface 26 of the distal end 24, and the tool guide hole 32 is the end of a tool route 32A. The tool route 32A is connected to a is channel opening 32C in FIG. 1 through a connecting pipe 32B and a flexible tube (not shown). This forms a tool channel from the channel opening 32C to the tool guide hole 32.

A nozzle 34 for jetting a washing liquid toward the observation window 28 is also provided on the end surface 26 of the distal end 24. The nozzle 34 is fitted on a liquid supply opening 36 formed in the end surface 26, and its liquid jetting opening 38 faces the observation window 28. The washing liquid jetted from the liquid jetting opening 38 flows on the observation window 28 to wash it, and then the washing liquid is discharged to the outside through a slit 11 of the cap 10. A cut 11A shown by a two-dot chain line in FIG. 4 may be formed instead of the slit 11. The slit 11 or the cut 11A improves the fit of the cap 10 on the distal end 24 by allowing air to come out through the slit 11 or the cut 11A. The endoscope 12 is a direct-vision endoscope with which the operator observes the body along the axis of the insertion part 16, but a side-vision endoscope may be used. In this case, a flat part is formed on the side of its distal end and the above-described parts are formed on the flat part.

The object lens unit 31 in FIG. 3 is composed of an object optical system (observation optical system) 40 and an imaging unit 42. The object optical system 40 has an object lens 48, movable lenses 58 and 60 a relay lens 61 and a prism 50 that changes a direction of an object light by 90° in a lens barrel 46. Movement of the movable lenses 58 and 60 along an optical axis changes a focal length of the object optical system 40.

The movable lenses 58 and 60 are held by lens frames 62 and 64, respectively, and the lens frames 62 and 64 are supported in such a manner as to move along a guide groove (not shown) of the lens barrel 46 along the optical axis. Cam pins (not shown) are provided on the lens frames 62 and 64, and coupled with cam grooves formed on the outer periphery of a rod cam (not shown). Rotation of the rod cam by hand or a motor (not shown) moves the lens frames 62 and 64 along the cam groove along the optical axis. The lens barrel 46 is fixed to a block 44.

The imaging unit 42 has a solid-state imaging device 54 including a CCD mounted on a substrate 52. The solid-state imaging device 54 is fixed to the prism 50, and the object optical system 40 forms the object image on a receiving surface of the prism 50. A number of wires are connected to the substrate 52, and the wires are bundled into a cable 56. The cable 56 extends to the universal code 18 through the insertion part 16 and the hand control part 14, and connects to the processor through a connector (not shown) at the end of the universal code 18. Image signals of the object captured by the solid-state imaging device 54 are processed by an image processing part of the processor, and an image of the object is displayed on a monitor (not shown).

Figure 4:
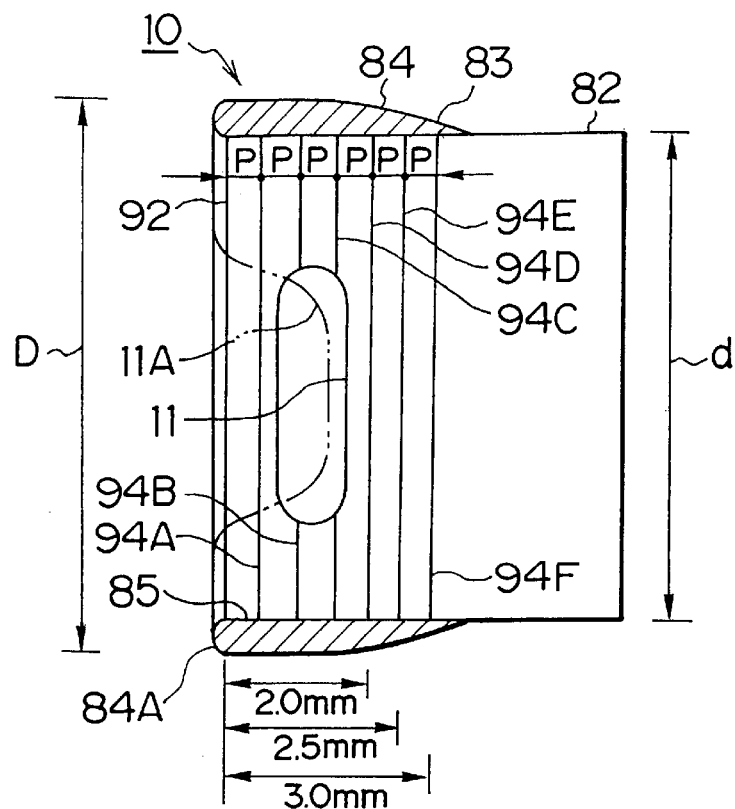
FIG. 4 is a section of a cap fitted on the endoscope in FIG. 1.

As shown in FIGS. 3 and 4, the cap 10 is substantially shaped like a cylinder. The cap 10 is made from transparent synthetic resin with a predetermined hardness such as vinyl chloride resin and polyurethane resin, so that it does not interfere the observation with the object lens unit 31 and it does not deform even when it is pushed against a mucous membrane or the mucous membrane is absorbed. The cap 10 is composed of a thin peripheral part 82 and a thick end part 84, and they are connected through a gentle curved part 83 so that the thickness does not dramatically change at the border between them.

The peripheral part 82 is fitted on an adhesive part 86 formed on the outer periphery of the distal end 24. The adhesive part 86 is an adhesive for fixing a bending rubber 88 of the distal end 24 and the bending part 22 to the block 44. A reference numeral 90 denotes a string for tying the bending rubber 88 to the block 44.

An outer diameter d of the peripheral part 82 of the pre-fitted cap 10 is a little smaller than an outer diameter D of the end part 84 as shown in FIG. 4. An outer diameter of the peripheral part 82 of the fitted cap 10 is substantially the same as the outer diameter of the end part 84 as shown in FIG. 3 to reduce pain to the patient when the insertion part 16 is inserted into or drawn from the body. The peripheral part 82 is hard so as to be firmly fitted on the distal end 24.

Figure 5:
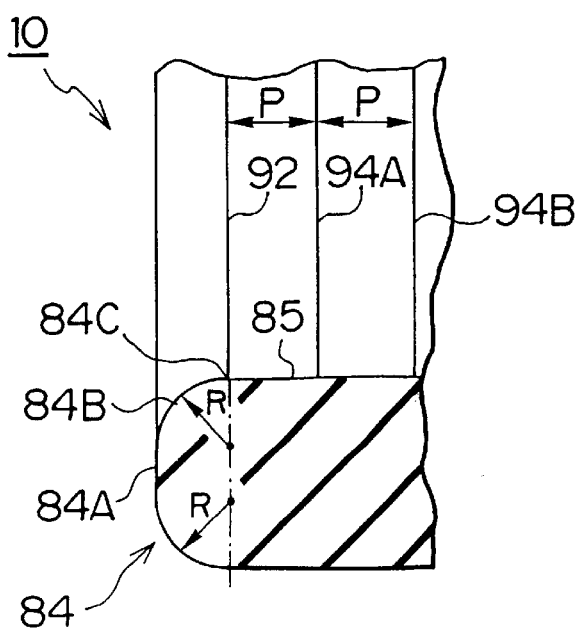
FIG. 5 is an enlarged section of an essential part of the cap in FIG. 4.
Figure 6:
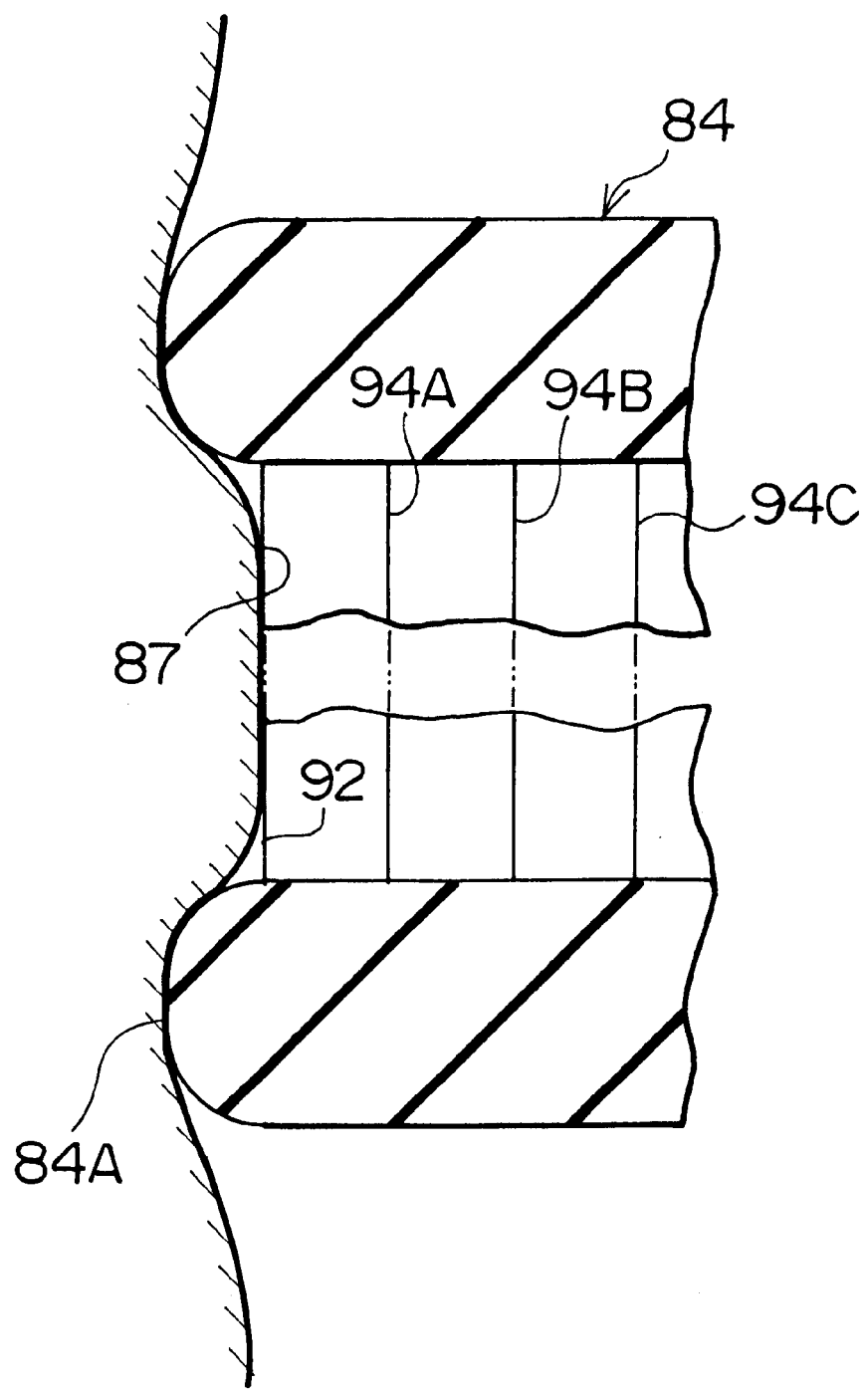
FIG. 6 is an explanatory view of a swelling mucous membrane when the cap is pressed against it.

The end part 84 is a predetermined length ahead of the end surface 26 of the distal end 24, and a circular end surface 84A in FIGS. 5 and 6 comes in contact with the mucous membrane 87 or the like. The end part 84 is softer than the peripheral part 82 not to damage the mucous membrane 87. The hardness of the parts 82 and 84 of the cap 10 can be adjusted according to the amounts of curing agent, crosslinking agent and plasticizer. For example, the curing agent raises the hardness and the plasticizer lowers it. In addition, even when the end part 84 is pressed against the mucous membrane 87, the end part 84 absorbs the pressing force by elastically deforming to reduce pain to the patient.

A reference mark 92 and six marks 94A, 94B, 94C, 94D, 94E and 94F are formed on an inner periphery 85 of the end part 84 with regular intervals P. The reference mark 92 shows an ideal focus position, and the marks 94A, 94B, 94C, 94D, 94E and 94F are laid down at the determinate distances P on the inner periphery 85 of the cap behind the ideal focus position.

The reference mark 92 is a length R behind of the circular end surface 84A. The reason why the ideal focus position is not at the circular end surface 84A but the reference mark 92 is as follows. When the circular end surface 84A is pressed against the mucous membrane 87 as shown in FIG. 6, the mucous membrane 87 slightly swells toward the end surface 26 of the distal end 24 to be flush with a circular plane enclosed by the reference mark 92. In addition, since the section of the circular end surface 84A is ark-shaped with the radius of curvature R, the mucous membrane 87 is not damaged even when the circular end surface 84A is pressed against it. Moreover, pulsation motion of the patient does not affect the observation since the end part 84 holds the mucous membrane 87 by pressing the circular end surface 84A against it.

For example, the intervals P of the marks 94A–94F are 0.5 mm. When the end surface 26 of the distal end 24 is on the mark 94A, the distance between the observation window (object optical system) 28 and the mucous membrane 87 is 0.5 mm. The distances between them are 1.0, 1.5, 2.0, 2.5 and 3.0 mm when the end surface 26 is on the marks 94B–94F, respectively. The marks 92 and 94A–94F may be grooves or swells, and they may be printed.

The operation of the endoscope 12 will now be explained.

The object optical system 40 is focused with 70× magnifications when the distance between the observation window 28 and the mucous membrane 87 is 3.0 mm, and it is focused with 80× magnifications when the distance between them is 2.5 mm, and it is focused with 100× magnifications when the distance between them is 2.0 mm.

For the 70× magnifications, the end surface 26 of the distal end 24 is on the mark 94F. Then, the circular end surface 84A is pressed against the mucous membrane 87 to swell it to the reference mark 92 (the ideal focus position) as shown in FIG. 6. Thus, the object optical system 40 is focused on the mucous membrane 87.

As described above, the position to which the mucous membrane 87 swells when the circular end surface 84A is pressed against it is set as the ideal focus position, and the end part 84 holds the mucous membrane 87. Thus, the mucous membrane 87 does not come off the ideal focus position due to the pulsation motion of the patient.

Therefore, the endoscope 12 can hold the mucous membrane 87 at the ideal focus position without being affected by the pulsation motion of the patient and all other movement.

Since the end part 84 is softer than the peripheral part 82, the end part 84 softly comes in contact with the mucous membrane 87 to protect it. There is no step between the peripheral part 82 and the end part 84, and the there is such a small step (see FIG. 3) between the peripheral part 82 and the bending rubber 88 that the cap 10 does not become lodged in the patient's body. Thus, the insertion part 16 of the endoscope 12 can be smoothly inserted into and drawn from the patient's body, and this makes it easier to operate the endoscope 12.

The endoscope 12 is operated in the same way for the 80× magnifications and the 100× magnifications.

The six marks 94A–94F are formed with the intervals of 0.5 mm in the embodiment, but the number and the intervals of the marks may be changed according to the type of the endoscope.

As described above, according to the endoscope of the present invention, the position to which the object swells when the cap is pressed against it is set as the ideal focus position. Thus, the object optical system can be focused on the object without being affected by the pulsation motion of the patient and all other movement.

As described above, according to the endoscope cap of the present invention, the peripheral part is thinner than the end part, and the outer diameter of the peripheral part is smaller than that of the end part before the cap is fitted, and the outer diameter of the peripheral part is substantially the same as that of the end part after the cap is fitted. Thus, there is no step between the peripheral part and the end part, and the insertion part of the endoscope can be smoothly inserted into and drawn from the patient's body.

In addition, since the end part is softer than the peripheral part, the object is not damaged. Even when the end part is pressed against the mucous membrane, the end part absorbs the pressing force by elastically deforming to reduce the pain to the patient.

It should be understood, however, that there is no intention to limit the invention to the specific forms disclosed, but on the contrary, the invention is to cover all modifications, alternate constructions and equivalents falling within the spirit and scope of the invention as expressed in the appended claims.

What is claimed is:

1. An endoscope, comprising:
   an insertion part;
   an object optical system arranged in a distal end of the insertion part, the object optical system changing a focal length thereof;
   a cap fitted on an outer periphery of the distal end of the insertion part; and
   a series of marks laid down on an inner periphery of the cap, each mark on which the distal end of the insertion part is positioned corresponding to a respective magnification of an object to be observed,
   wherein the object is pressed and swollen within the cap to be observed and the ideal focus position for the object optical system is a predetermined length behind a distal end of the cap.

2. The endoscope as set forth in claim 1, wherein a section of an edge part of the distal end of the cap is ark-shaped with a radius of curvature of the predetermined length.

3. The endoscope as set forth in claim 1, wherein the series of marks are laid down at determinate distances on the inner periphery of the cap behind the ideal focus position.

4. The endoscope as set forth in claim 1, wherein the cap comprises:
   a peripheral part which is to be on the outer periphery of the distal end; and
   an end part which comes in contact with an object, wherein:
   the peripheral part is thinner than the end part;
   an outer diameter of the peripheral part is smaller than an outer diameter of the end part before the endoscope cap is fitted on the outer periphery of the distal end; and
   the outer diameter of the peripheral part is substantially equal to the outer diameter of the end part after the endoscope cap is fitted on the outer periphery of the distal end.

5. The endoscope cap as set forth in claim 4, wherein the end part is softer than the peripheral part.

* * * * *